United States Patent [19]

Günther

[11] Patent Number: 5,198,549
[45] Date of Patent: Mar. 30, 1993

[54] SIDE-CHAIN CHLORINATION OF ALKYLATED NITROGEN HETEROAROMATICS

[75] Inventor: Andreas Günther, Cologne, Fed. Rep. of Germany

[73] Assignee: Bayer Aktiengesellschaft, Leverkusen, Fed. Rep. of Germany

[21] Appl. No.: 699,059

[22] Filed: May 13, 1991

[30] Foreign Application Priority Data

May 19, 1990 [DE] Fed. Rep. of Germany ....... 4016175

[51] Int. Cl.$^5$ ................. C07D 213/26; C07D 213/61; C07D 239/26; C07D 239/30
[52] U.S. Cl. .................................. 546/345; 546/346; 544/334; 544/242
[58] Field of Search ................. 546/345, 346; 544/334

[56] References Cited

U.S. PATENT DOCUMENTS 4,788,896  10/1988  Gallenkamp .................. 546/304

FOREIGN PATENT DOCUMENTS 0012108  6/1980  European Pat. Off. ............ 546/304
0260485  3/1988  European Pat. Off. ............ 546/345
1470064  5/1969  Fed. Rep. of Germany ...... 546/346

Primary Examiner—Alan L. Rotman
Attorney, Agent, or Firm—Sprung Horn Kramer & Woods

[57] ABSTRACT

In the chlorination of the side chain of an alkylated nitrogen heteroaromatic such as pyridine or pyrimidine by reaction with elemental chlorine, the reaction is effected in acetonitrile as solvent.

3 Claims, No Drawings

SIDE-CHAIN CHLORINATION OF ALKYLATED NITROGEN HETEROAROMATICS

It is known to react the side chains of alkylated nitrogen heteroaromatics, in particular of alkylated pyridines, with chlorine, one or more hydrogen atoms being substituted by chlorine atoms. It is additionally known to influence the rate and yield of this reaction favorably by free radical-initiating radiation or by chemical free radical initiators. Finally, it is known that the use of a solvent for this reaction is often favorable, for example because the reaction product is solid at the selected reaction temperature or because the solvent increases the yield.

The choice of this solvent is problematical, however. Hydrocarbons are hardly suitable as they usually react themselves with the chlorine employed. Chlorohydrocarbons, on the other hand, in particular carbon tetrachloride, have often been used (see, for example, Chemical Abstracts 84 (17): 121665p). For ecological and toxicological reasons, however, these solvents become problematical substances to an increasing extent for industrial practice. Finally, inorganic substances, for example concentrated sulphuric acid or chlorosulphonic acid (see DE-A 1,470,064) have also already been proposed as solvents. The problem here, however, is that large amounts of strongly polluted waste water are produced when working up the reaction mixture.

There was therefore a need to find a chlorine-free solvent for the reaction mentioned, which, like carbon tetrachloride, similarly favorably influences the side-chain chlorination of nitrogen heteroaromatics and can be recovered after the reaction to a large extent by simple distillation. In this way, the disadvantages described above of the processes described hitherto should be avoided.

Surprisingly, it has now been found that particularly favorable results are achieved in the chlorination of the side chains of alkylated nitrogen heteroaromatics with elemental chlorine if acetonitrile is used as the solvent.

This is both surprising because the methyl group of the acetonitrile would be expected to react like the alkyl side chain of the nitrogen heteroaromatic, with chlorine (see, for example, DD-A 227,134, U.S. Pat. No. 3,825,581 or U.S. Pat. No. 3,418,228), and because Comparison Experiments 5 to 8 hereinbelow show that acetonitrile is far less favorable solvent than, for example, carbon tetrachloride in the chlorination of the alkyl side chain of other aromatics.

The advantage of the process according to the invention is that a solvent is employed which, compared to the chlorinated hydrocarbons, for example carbon tetrachloride, is far more favorable with respect to ecology and carcinogenicity and which in relation to reaction rate, yield and recoverability has similar, in some cases even better properties, than carbon tetrachloride (for this see Comparison Examples 2 to 4). There are also great advantages as regards the possibility of carrying out the reaction solvent-free, as Comparison Example 1 shows.

To carry out the process according to the invention, a solution in acetonitrile is preferably used which contains 5 to 70% by weight of the alkylated nitrogen heteroaromatic to be chlorinated.

Possible alkylated nitrogen heteroaromatics are preferably alkylated pyridine or pyrimidine derivatives optionally containing further substituents. Those which may be mentioned by way of example are: 3-methyl-pyridine, 2-chloro-5-methyl-pyridine, 2,4-dichloro-6-methyl-pyridine, 2,4-dichloro-6methyl-pyrimidine and 2-ethyl-pyridine. 2-Chloro-5-methyl-pyridine is particularly preferably employed as a starting component in the process according to the invention.

The reaction temperature of the process according to the invention is preferably 50° C. to 150° C. and the reaction pressure 0.3 to 5.0 bar. Temperature and pressure are particularly preferably adjusted such that reflux conditions are established.

The reaction can be controlled by variation of the conditions, for example the period of introduction of the chlorine gas, such that single or multiple chlorination of the alkyl side chain occurs.

The process according to the invention is preferably carried out in the presence of free radical-initiating radiation, such as, for example, UV light, or of free radical-initiating substances, such as, for example, azobiscarbonitriles or diacyl peroxides. If the target molecule is a monochloromethyl compound, the reaction is preferably carried out with free radical-initiating substances, as it has surprisingly been found that they are clearly superior to UV light in this case (see Examples 1 and 2).

The determination of the end point of the reaction is carried out by conventional methods, for example the reaction mixture is analyzed during the reaction by gas chromatography and the addition of chlorine is terminated as soon as the content in the desired product has reached its maximum. In this case, it may also be advantageous to terminate the reaction before this maximum, to recover the unreacted starting material and to employ it again in the reaction.

The reaction mixture is worked up by conventional methods, for example the acetonitrile is removed by distillation in vacuo and employed again in the reaction. Recovery rates of 95% to 98% are achieved here. The distillation bottom is then rendered neutral at room temperature using sodium hydroxide solution. The organic phase is separated off and the product is isolated in vacuo by rectification. The forerun from the rectification may still contain starting material, which can be recycled.

The process according to the invention is further illustrated by the following examples.

EXAMPLE 1

Preparation of 2-chloro-5-chloromethylpyridine

1 Mol of 2-chloro-5-methylpyridine and 128 g of acetonitrile are heated to reflux at normal pressure. 0.2 g of azobisisobutyronitrile is added as a free radical initiator and this addition is repeated every half hour. Chlorine gas is simultaneously introduced in a slight excess and the reaction mixture is furthermore kept continuously at reflux. After 4 hours, the reaction is terminated. The solvent is removed by distillation at a bottom temperature of about 85° C. by slowly applying vacuum. 122 g are recovered, which can be fed back into the next batch. 0.37 Mol of product and 0.53 mol of starting material are isolated from the bottom. Based on the reacted starting material (0.47 mol), a yield of 79% thus results.

COMPARISON EXAMPLE 1

Shows that the solvent-free preparation of 2-chloro-5-chloromethylpyridine is unfavorable:

Chlorine gas is introduced at 85° C. in a slight excess into 1 mol of 2-chloro-5-methylpyridine. At the beginning and then after each half hour, 0.2 g of azoisobutyronitrile is added. After 4 hours, only 0.2 mol of product has been formed.

COMPARISON EXAMPLE 2

Shows the preparation of 2-chloro-5-chloromethylpyridine in carbon tetrachloride:

1 Mol of 2-chloro-5-methylpyridine and 128 g of carbon tetrachloride are heated to reflux. 0.2 g of azobisisobutyronitrile is added and this addition is repeated every half hour. Chlorine gas is simultaneously introduced in a slight excess. After 3 hours, the reaction is terminated and 0.37 mol of product and 0.53 mol of starting material are isolated.

EXAMPLE 2

Preparation of 2-chloro-5-chloromethylpyridine

1 Mol of 2-chloro-5-methylpyridine and 128 g of acetonitrile are heated to reflux. The mixture is irradiated with UV light and chlorine gas is introduced in a slight excess. The reaction is terminated as soon as 0.37 mol of product has been formed. 0.46 Mol of starting material is simultaneously recovered. Based on the reacted starting material, a yield of 69% results.

EXAMPLE 3

Preparation of 2,4-dichloro-6-chloromethylpyrimidine

1 Mol of 2,4-dichloro-6-methylpyrimidine and 326 g of acetonitrile are heated to reflux. 0.12 g of azobisisobutyronitrile is added and this addition is repeated every half hour. Chlorine gas is simultaneously introduced in a slight excess. After 0.75 hours, the reaction is terminated and 0.51 mol of product is obtained in addition to 0.31 mol of starting material according to gas-chromatographic analysis (yield 74%).

COMPARISON EXAMPLE 3

Shows the preparation of 2,4-dichloro-6-chloromethylpyrimidine in carbon tetrachloride:

1 Mol of 2,4-dichloro-6-methylpyrimidine and 326 g of carbon tetrachloride are heated to reflux. 0.12 g of azobisisobutyronitrile is added and this addition is repeated every half hour. Chlorine gas is simultaneously introduced in a slight excess. After 1.1 hours, the reaction is terminated and 0.51 mol of product is obtained in addition to 0.31 mol of starting material.

EXAMPLE 4

Preparation of 2,4-dichloro-6-dichloromethylpyrimidine

The procedure is as in Example 3, but the reaction is ended after 3 hours. 0.71 Mol of product is obtained in addition to 0.19 mol of 2,4-dichloro-6-chloromethylpyrimidine. The latter can be fed back into the process so that a yield of 88% results.

COMPARISON EXAMPLE 4

Shows the preparation of 2,4-dichloro-6-dichloromethylpyrimidine in carbon tetrachloride:

The process is as in Comparison Example 3, but the reaction is ended after 3.75 hours. 0.71 Mol of product is obtained in addition to 0.19 mol of 2,4-dichloro-6-chloromethylpyrimidine.

Comparison Examples 5 to 8 compare the solvents acetonitrile and carbon tetrachloride for the side-chain chlorination of aromatics not containing nitrogen.

COMPARISON EXAMPLE 5

Preparation of 2,4-dichloro-chloromethylbenzene

1 Mol of 2,4-dichloro-methylbenzene and 322 g of carbon tetrachloride are heated to reflux. 0.8 g of azobisisobutyronitrile is added and chlorine gas is introduced in a slight excess. After 0.5 hours, 0.75 mol of product is obtained according to gas-chromatographic analysis.

COMPARISON EXAMPLE 6

Preparation of 2,4-dichloro-chloromethylbenzene

1 Mol of 2,4-dichloro-methylbenzene and 322 g of acetonitrile are heated to reflux. 0.8 g of azobisisobutyronitrile is added and this addition is repeated every half hour. Chlorine gas is simultaneously introduced in a slight excess. 0.75 Mol of product is obtained after 2 hours.

COMPARISON EXAMPLE 7

Preparation of 1,4-bis-trichloromethylbenzene

1 Mol of 1,4-dimethylbenzene and 1,000 g of carbon tetrachloride are heated to reflux. 0.2 g of azobisisobutyronitrile is added and this addition is repeated every half hour. Chlorine gas is simultaneously introduced in a slight excess. The reaction is terminated after 18 hours and 0.9 mol of product can be isolated.

COMPARISON EXAMPLE 8

Preparation of 1,4-bis-trichloromethylbenzene

The reaction is carried out as in Comparison Example 7, but using 1,000 g of acetonitrile instead of carbon tetrachloride. Even after a reaction period of 18 hours, no product has been formed.

It will be understood that the specification and examples are illustrative but not limitative of the present invention and that other embodiments within the spirit and scope of the invention will suggest themselves to those skilled in the art.

What is claimed is:

1. In the chlorination of the wide chain of an alkylated pyridine or pyrimidine with elemental chlorine, the improvement which comprises effecting the reaction in acetonitrile as solvent in the presence of free radical-initiating radiation or of a chemical free radical initiator selected from the group consisting of azobiscarbonitrile and a diacyl peroxide.

2. The process according to claim 1, wherein the reaction is effected under reflux.

3. The process according to claim 1, wherein 2-chloro-5-methylpyridine is reacted to give 2-chloro-5-chloromethylpyridine.

* * * * *

UNITED STATES PATENT AND TRADEMARK OFFICE
CERTIFICATE OF CORRECTION

PATENT NO. : 5,198,549
DATED : March 30, 1993
INVENTOR(S) : Andreas Gunther

It is certified that error appears in the above-indentified patent and that said Letters Patent is hereby corrected as shown below:

On the title page: Item[56] U.S. Patent Documents: Delete "4,788,896" and substitute -- 4,778,896 --.

Column 4, line 54, Delete "wide" and substitute --side --.

Signed and Sealed this

Sixth Day of September, 1994

Attest:

BRUCE LEHMAN

Attesting Officer

Commissioner of Patents and Trademarks